United States Patent [19]

Calkin

[11] Patent Number: 5,027,833
[45] Date of Patent: Jul. 2, 1991

[54] EXTRICATION AND SPINAL RESTRAINT DEVICE

[76] Inventor: Carston R. Calkin, P.O. Box 230487, Tigard, Oreg. 97223

[21] Appl. No.: 490,006

[22] Filed: Mar. 6, 1990

[51] Int. Cl.$^5$ ............................................. A61F 5/37
[52] U.S. Cl. .................... 128/870; 128/846; 128/869; 128/874; 2/44
[58] Field of Search ............... 128/846, 869, 870, 874, 128/78, 87 B, 87 R, 89 A; 2/44; 5/82

[56] References Cited

U.S. PATENT DOCUMENTS

| | | | |
|---|---|---|---|
| 4,400,820 | 8/1983 | O'Dell et al. | 128/869 X |
| 4,589,407 | 5/1986 | Koledin et al. | 128/869 |
| 4,593,788 | 6/1986 | Miller | 128/869 X |
| 4,665,908 | 5/1987 | Calkin | 128/870 |
| 4,776,327 | 11/1988 | Russell | 5/82 R X |
| 4,899,736 | 2/1990 | Nesbitt | 128/870 X |

Primary Examiner—Robert A. Hafer
Assistant Examiner—Brian E. Hanlon
Attorney, Agent, or Firm—Olson & Olson

[57] ABSTRACT

An extrication and spinal restraint device for use in emergency rescues, an onsite medical aid where potential back, neck and shoulder injuries may exist includes a jacket of flexible material arranged to extend the entire length of a victim's spine, neck and head and be secured thereto by head, torso and pelvic straps, the jacket mounting a pair of rigid backboard members arranged to be disposed behind a victim's back, neck and head and configured to extend with the confronting longitudinal edges disposed along a victim's spine to provide rigid support only inwardly of the sides of a victim's body and head, the pelvic straps configured and disposed specifically to engage the pelvic structure of a human torso specifically above the articulating joints of the hips, so that movement of the legs is permitted without affecting changes in tension on the jacket, and the head is positively immobilized by a pair of straps configured specifically to engage only the fixed, non-articulating portion of a human skull or a rigid cervical collar if provided.

11 Claims, 3 Drawing Sheets

EXTRICATION AND SPINAL RESTRAINT DEVICE

BACKGROUND OF THE PRIOR ART

This invention relates to backboards used in emergency extrications where possible back, neck and spine injuries may exist, and more particularly to a greatly improved construction over my earlier device, identified in U.S. Pat. No. 4,665,908, issued 19 May 1987.

My earlier extrication and spinal restraint device represents the closest relevant art pertaining to the present invention, this new device incorporating various important structural modifications which provide for a greatly improved, safer and more versatile extrication and spinal restraint apparatus.

Emergency backboards are commonplace and are necessary and very frequently used tools by emergency medical aid units. Their purpose is to be applied to a victim injured in an accident whereby to immobilize the spine, neck and head when such injuries appear to be indicated. Upon immobilizing a victim, rescuers may then extricate him from the site of the injury, transport him to a stretcher, and take him to a medical provider for treatment without concern that such movement may intensify those serious injuries. Illustrative of other typical backboards, spinal restraints and extrication devices known in the art are U.S. Pat. Nos. 4,211,218; 4,299,211; 4,259,950; and 3,889,668.

While my earlier extrication and spinal restraint construction was very advantageous over those devices previously known, I have found that various limitations and disadvantages exist which reduce the overall effectiveness of my device was reduced in certain types of emergency extrication and restraint situations involving certain types of injuries. Accordingly, it became evident that a need was experienced for changes which would overcome the limitations and disadvantages of my earlier construction.

SUMMARY OF THE INVENTION

In its basic concept, the extrication and spinal restraint device of this invention utilizes a flexible jacket of material configured to be wrapped partially around a victim's torso and be secured thereabout by two adjustable torso straps, the jacket mounting a pair of longitudinally elongated, tapered, inflexible back brace boards configured to extend from behind the head to the base of the spine along the center line of the victim's back, neck and head, the flexible jacket mounting a pair of shoulder straps and a pair of pelvic straps, and a pair of head flaps configured to partially encircle a victim's head, whereby a pair of releasable head support straps may be releasably secured to engage and hold a victim's head immovably during extrication in transport.

It is by virtue of the foregoing basic concept that the principal objective of this invention is achieved; namely, the provision of an improved extrication and spinal restraint device of the class described which overcomes the limitations and disadvantages of the restraint device of my earlier invention.

Another object of this invention is the provision of a spinal restraint device of the class described which utilizes lower pelvic straps that are configured for positioning and securing substantially above and about the articulating portion of the hips, so that movement of the legs during extrication and transport cannot effect any changes on the tension of the lower straps connected to the jacket, and hence movement of the legs does not result in movement of the restraint device relative to the upper body and neck of a victim which can cause movement of the injured spine.

Another object of this invention is the provision of a spinal restraint device of the class described which mounts a pair of upper shoulder straps that are configured for both crossover connection across the upper chest, and for single side connection over individual shoulders for retraction of fractured clavicle.

A still further object of this invention is the provision of a spinal restraint device of the class described which includes a lower head strap configured for attachment to the head flaps of the jacket, the lower head strap arranged to engage the lower fixed portion of the skull of a victim or to engage a rigid neck injury collar if so provided, to secure the lower head firmly in position without limiting the patient's jaw movement for talking, breathing, and in case of vomiting during immobilization.

The foregoing and other objects and advantages of this invention will appear from the following detailed description, taken in connection with the accompanying drawings of a preferred embodiment.

DESCRIPTION OF THE PREFERRED EMBODIMENT

Figure 4:
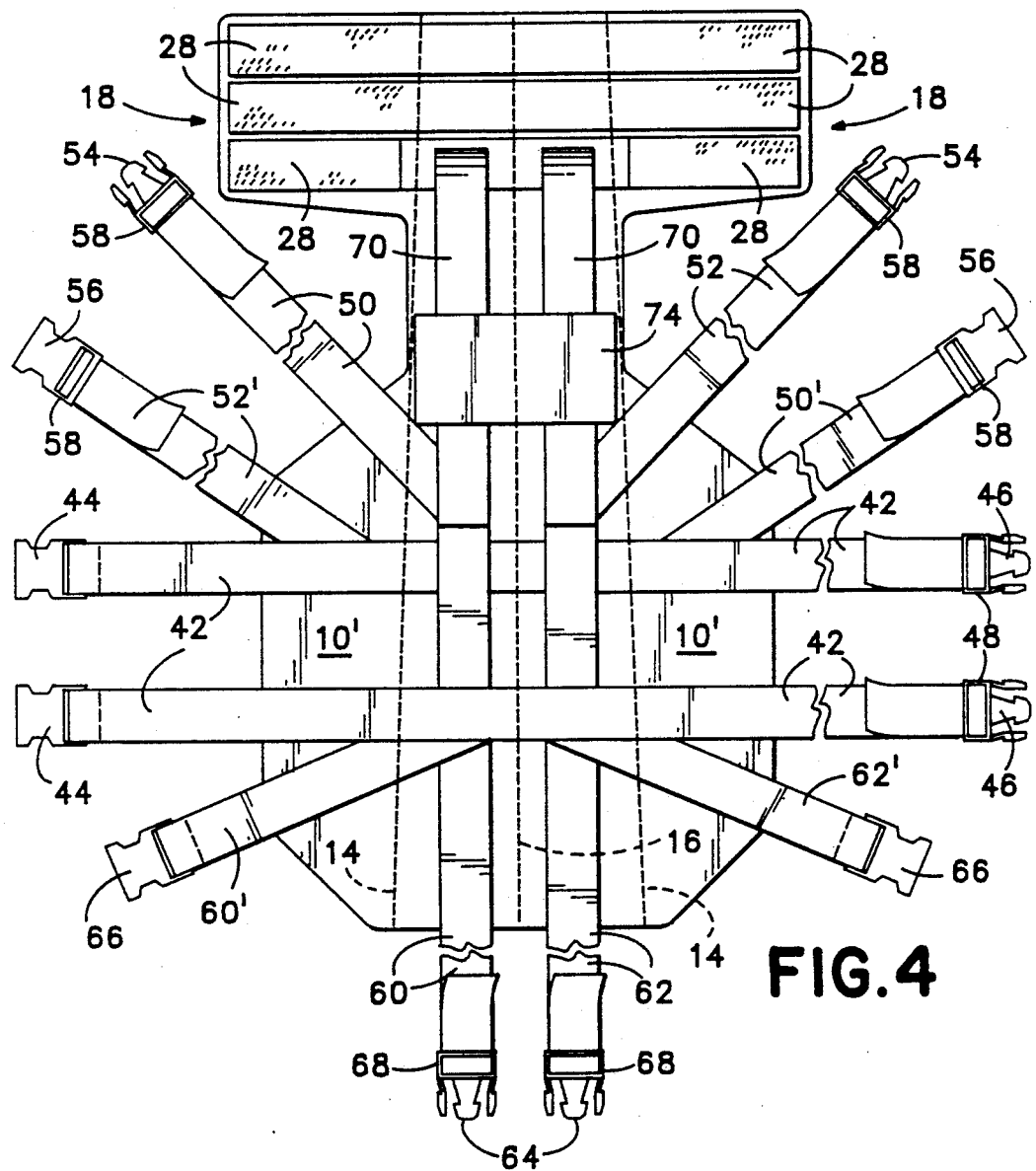
FIG. 4 is a foreshortened, plan view of the rear side of the extrication and spinal restraint device seen in FIG. 2, but in open, flat condition.
Figure 5:
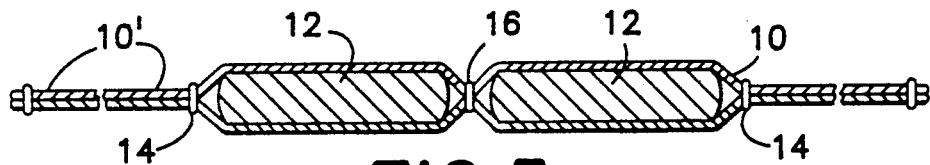
FIG. 5 is a foreshortened sectional view of the midportion of the spinal restraint device of this invention showing the rigid backboards, their associated pockets in the jacket, and the corresponding stitching as shown in FIG. 4.

Like my earlier extrication and spinal restraint device, this invention comprises a jacket 10, shown best in FIG. 4, of reinforced cloth, plastic or other strong but flexible material, and contains a pair of rigid, longitudinally elongated back support boards 12 in a pair of pockets formed by side and central stitchings 14, 16 through the flexible jacket material, as seen best in FIGS. 4 and 5. In this regard, the pockets may be formed by stitching an additional layer of material onto the jacket in appropriate position, or the entire jacket may be formed of two identical sheets of material with stitching provided about their edges to attach them together and also stitching to form the desired pockets for maintaining the backboards 12 in proper position.

The back support members thus render the central portion of the jacket body 10 rigid. The portions of the jacket disposed on opposite lateral sides of the rigid central portion defined by the side stitchings 14 are devoid of stiffening members and form lateral torso side flaps 10' which are longitudinally and laterally freely flexible for purposes which will become evident later.

Figures 1, 2:
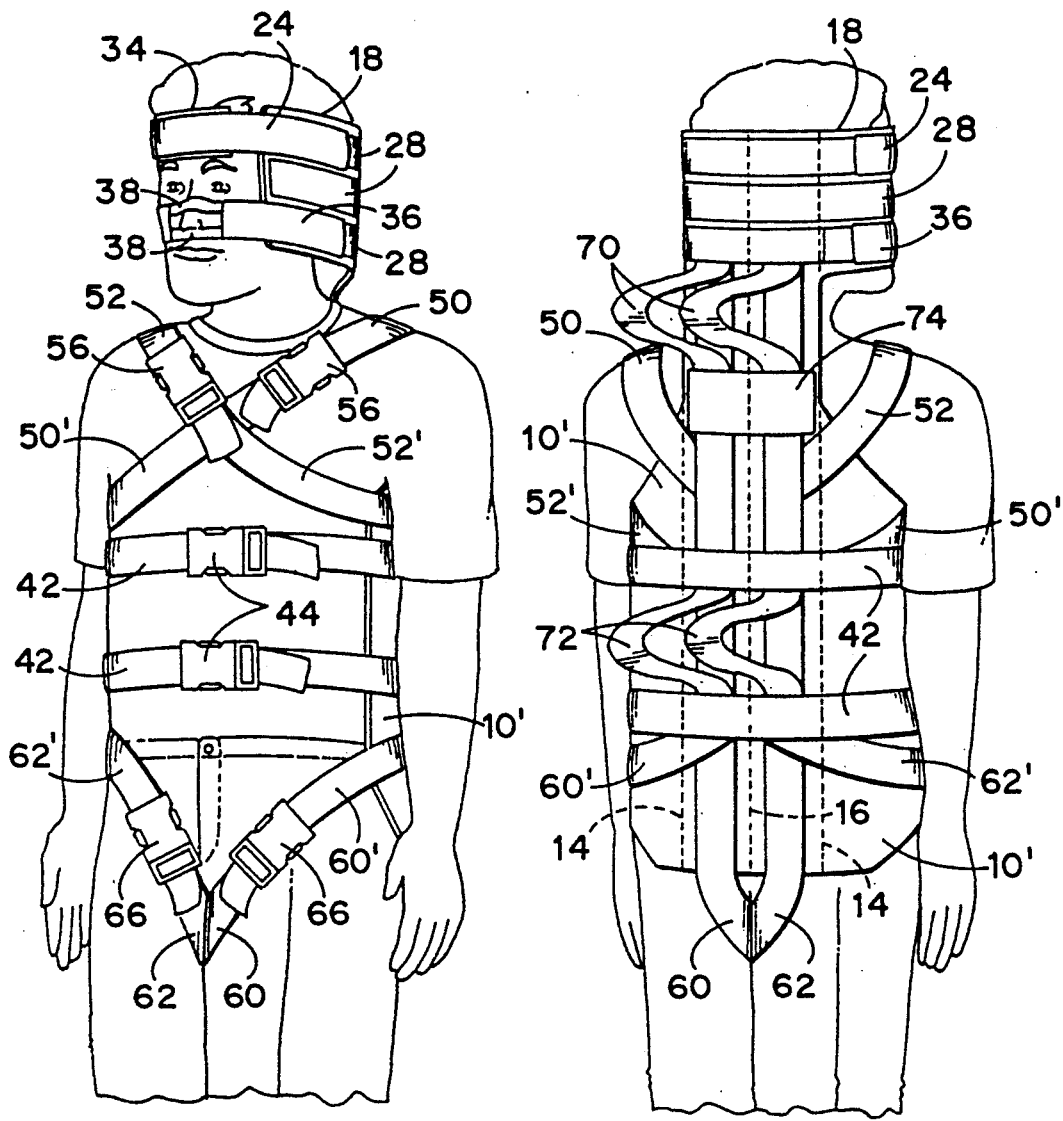
FIG. 1 is a fragmentary perspective front view of an extrication and spinal restraint device embodying the features of this invention on a victim.
FIG. 2 is a fragmentary perspective view of the extrication and the spinal restraint device of FIG. 1 as would be viewed from the rear in FIG. 1.

The backboards are of sufficient length to support the entire length of the spine and head, as shown in FIGS. 1 and 2, each backboard is positioned to extend along the center stitch line of the jacket which is disposed substantially along the spine of the patient. As is apparent in FIG. 4, the outer lateral edges of the boards are preferably tapered inwardly from bottom to top, so that the width of the boards positioned behind the head and the neck is less than the width of the boards at the bottom of the jacket.

Figure 3:
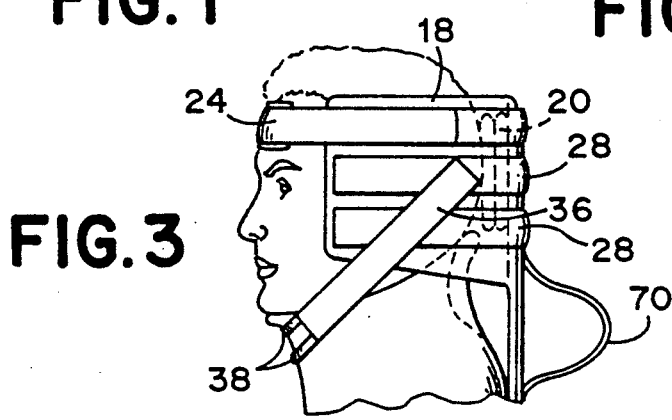
FIG. 3 is a fragmentary side elevation of the upper, head supporting portion of the spinal restraint device of this invention, detail otherwise hidden from view shown in broken lines the victim having a cervical collar applied.
Figure 6:
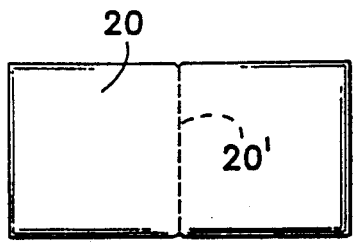
FIG. 6 and 7 are plan views of a set of foam head pads configured for placement behind the head of a victim as seen in broken lines in FIG. 3 of the drawings, FIG. 6 showing a double pad configuration arranged for folding to form a double thickness pad, and FIG. 7 showing a single pad.
Figure 7:
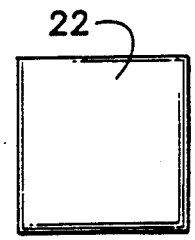

As seen best in FIG. 4 of the drawings, the jacket material 10 is widened in the head area in order to provide a pair of flexible head side support flaps 18 which fold forwardly about the sides of a patient's head, as in FIGS. 1, 2 and 3 of the drawings. In most patients, the scapular is more posterior than the back of the head. This results in a space usually ranging from zero to two and ½ inches between the back of the head and the support boards. This void behind the head must be filled with a correct amount of padding so that securing the patient's head to the device will not force the head forward into flexion or cause the head to move rearwardly into hyperextension. In cases where there is a void between the back of an upright head and the backboards, the firm head pads 20, 22, shown in FIGS. 6 and 7, are utilized as illustrated in broken lines in FIG. 3. These pads are preferably approximately three-quarters inch thick, and are utilized as indicated. The embodiment of FIG. 6 is a double pad, which is configured to be folded along stitch line 20' to form a double thickness pad. The pads are, as described, firm in nature so that a head may be securely held thereagainst without significant compression of the pads which might result in slight movement of the head during transport.

As indicated, the flexible head support flaps 18 are able to be wrapped rather snugly against the side of a victim's head to prevent it from turning or otherwise being moved. Means is provided to secure a victim's head immovably in position between the head flaps and the back brace members. With reference primarily to FIGS. 1, 3, 8 and 9, head restraining means is provided by a pair of straps arranged to overlie the victim's forehead and the lower, fixed portion of the skull or, alternatively, over a rigid cervical collar C, if provided the victim.

Figure 8:
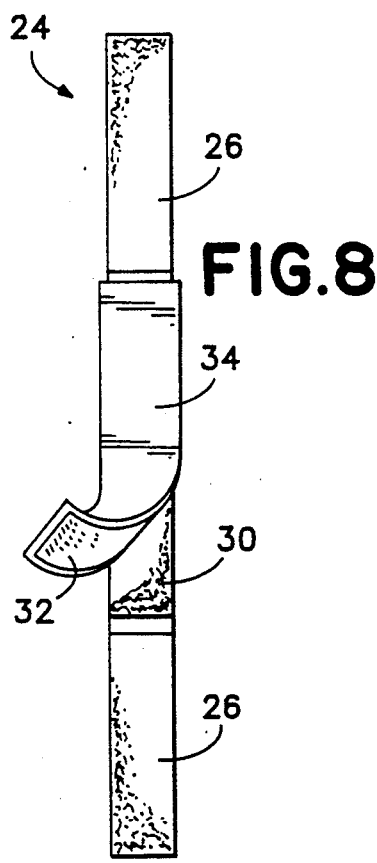
FIG. 8 is a plan view of a head restraining forehead strap mounting a removable and discardable forehead pad.

With reference first to the forehead strap 24 shown in FIG. 8, the strap comprises a length of material arranged to overlie a victim's forehead and a portion of each side support flap 18. As seen in FIG. 8, the opposite ends of the strap mount one component 26 of a conventional Velcro type hook and loop fastener, the other component 28 being provided on the outside surface of the head flaps 18. As also shown, the center portion of the strap preferably also mounts a Velcro type component 30 arranged to receive the corresponding component 32 provided on a removable and disposable open cell foam forehead pad 34. This pad is provided as a cushion between the forehead and the strap, and to prevent inadvertent slippage of the strap against the patient's forehead, and also to absorb perspiration during immobilization. These pads are preferably discarded after use, and replaced with a new one prior to another use.

Figure 9:
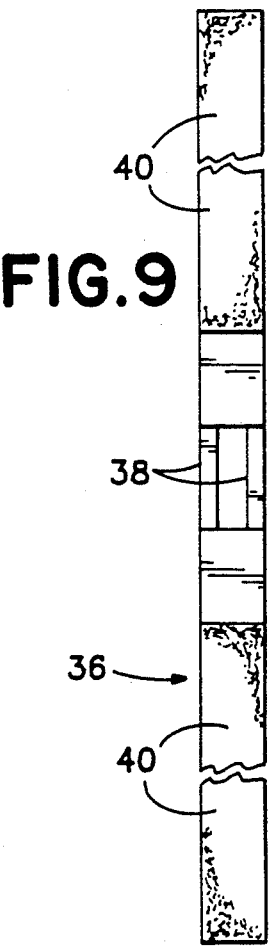
FIG. 9 is a plan view of a lower head restraining strap configured to engage and immovably hold the lower fixed portions of a patient's head securely to the device as shown in FIG. 1 and 3 of the drawings.

The lower headstrap 36, shown in FIG. 9, is provided to further secure the lower portion of the patient's head to the head portion of the jacket. The lower strap preferably comprises two lengths of material 36' connected together by a pair of spaced apart support strips 38. One component of a hook and loop fastener, preferably the loop component 40, is attached to one side surface of each of the two end lengths of material 36' for registry with the corresponding hook component 28 secured to the head support flap of the jacket.

FIGS. 1, 2 and 3 of the drawings illustrate the lower head strap in use on a patient whose injuries do not require the use of a cervical collar during extrication and immobilization (FIGS. 1 and 2), and in situations where a cervical collar is provided (FIG. 3). As seen in FIGS. 1 and 2, the spaced apart strips 38 joining the two end strap sections 36' together are configured to engage the lower, fixed portions of the skull by bridging the nose. In this manner, the patient's jaw movement is not restricted in any manner, although the head is restrained immovably against the backboards or the head pads 20, 22 between the head flaps 18. Alternatively, if a cervical collar is provided as in FIG. 3, the lower head strap 36 is instead positioned to encircle the front portions of the cervical collar C and is secured to the head flaps 18 of the jacket. In this manner, restraint of the lower head is provided by utilizing the rigid cervical collar already provided on a patient.

Means is also provided to secure the flexible torso flap portion 10' of the board supporting jacket onto an injured person so that the backboards are retained in proper position extending centrally along the victim's spine, the central stitching being disposed directly over the victim's spine. In this embodiment, a pair of chest straps 42 are provided at longitudinally spaced intervals along the torso portion of the jacket, and securely stitched to the flexible material. The upper torso strap is positioned approximately over the chest, and the lower torso strap is positioned in the area of the abdomen. Each strap includes corresponding fastening means, illustrated herein as buckle members 44, 46, and include adjustment means, illustrated herein as slide buckle 48 configured to adjust the length of the straps so that they may be brought snugly about a victim's torso. The purpose of the torso straps is merely to secure the jacket about the torso snugly so that the back is securely supported by the backboards, and do not otherwise function as a key element in the actual immobilization of the patient.

Means to immobilize the patient's upper body on the restraint device of this invention is provided by shoulder straps 50, 50' and 52, 52'. Each of these straps are secured, as by stitching, in an angular disposition to the upper portions of the flexible jacket side flaps 10', all preferably below the shoulders, so that the body is fully prevented from upward movement once secured. These shoulder straps 50, 50' and 52, 52' mount corresponding fastening means, illustrated herein as cooperating buckle members 54, 56, and adjustment means, illustrated herein as slide buckles 58 are provided to adjust the length of each strap member, whereby, aside from tightening adjustment, the straps may be adjusted to permit longitudinal adjustment of the patient on the spinal restraint device, to accommodate persons of different heights.

The illustrated configuration of shoulder straps provides the restraint device of this invention with an important dual function that provides appropriate restraint when upper thorax injuries are present and also when they are not. As will be understood from FIGS. 1 and 2 of the drawings, in the absence of upper thorax injuries, it is advantageous for the upper body to be secured by crossing the upper shoulder straps over the chest. In this regard, strap 50 is brought up and over the shoulder from behind the victim, while strap 50' is brought under the armpit on the opposite side, and then two straps are connected together crossing over the upper chest. Strap 52 and 52' are similarly connected, and all of the straps are then adjusted snugly. This crossover configuration provides a balanced upper body restraint, and prevents any tendency for the body to move side to side or up and down during immobilization.

In cases where upper thorax injuries may be indicated, such as a fractured clavical, it is desirable that the shoulder straps not cross over the upper anterior thorax, rather it is preferred that the shoulders be held back so that the patient is securely retained with the shoulders drawn rearwardly and widely, thus preventing compression of the clavicals. In these circumstances, the strap 50 is drawn up and over the shoulder and connected to the strap 52' which is drawn up under the armpit on the same side. The straps 52 and 50' are similarly attached on the other side of the patient. The connected straps are each positioned over the upper torso immediately inwardly of the shoulders, and hence do not put localized pressure on the clavical.

Means is provided to secure the lowermost fixed portion of the torso to the restraint device in a manner that leg movement will not effect movement or tension changes on the restraint device, and to prevent downward movement of the patient when secured to the device. In this regard, pelvic straps 60, 60' and 62, 62' are secured to the bottom of the jacket, the straps 60 and 62 being secured to the jacket extending substantially vertically over the backboard members and arranged to extend downwardly therefrom so that they may be brought from the rear of a patient forwardly between his legs to his front side. The straps 60', 62' are secured to the flexible side jacket material 10' and arranged to extend angularly downwardly, as seen in FIG. 4, so that they are directed around the pelvic girdle above the articulating leg sockets at the hip. Each strap mounts cooperating fastening and tension adjustment means, illustrated herein as cooperating buckle members 64, 66 and adjustment slide buckles 68.

In proper position, the lower straps 60, 62 are drawn between the legs and brought snugly up against the interconnecting, lower pelvic base bone structure, while the corresponding strap members 60', 62' are drawn about the sides of the pelvic girdle above the articulating hip joints. The corresponding fasteners are connected, and the straps are adjusted tightly in position. In this manner, with the pelvic straps securing the pelvis to the restraint device, the legs are free to articulate without affecting the tension applied against the lower straps, and hence the entire jacket. In order to minimize risk of further injury, the restraint device is preferably installed on a patient while he is still in the position that he was at the time of an accident. Oftentimes, this involves drivers and passengers in a car, and hence the restraint device is installed while the victim is still seated. Once the patient is immobilized, he is moved to a stretcher, and this process of extricating the patient clearly requires that the legs be free to move as the patient is moved from a sitting position to a laying position on a stretcher. Hence, every effort must be made to avoid placement of the pelvic straps about the legs. Accordingly, the side pelvic straps 60', 62' are positioned and secured to the jacket high enough so as to assure that they remain above the articulating socket of the hip.

In order to facilitate the victim's extrication and transport, the spinal restraint device of the present invention includes means engaging the rigid portion of the jacket whereby rescuers may safely lift and move a victim secured immovably to the device. As seen best in FIGS. 2 and 4, a pair of upper lifting straps 70 and lower lifting straps 72 are provided for this purpose. In this embodiment, the lifting straps are provided by forming loops in the upwardly extending straps 60, 62 which are provided to extend along and be secured to substantially the full length of the backboards. Other such handle means as may be desired or indicated may alternatively be utilized as well.

Figure 10:
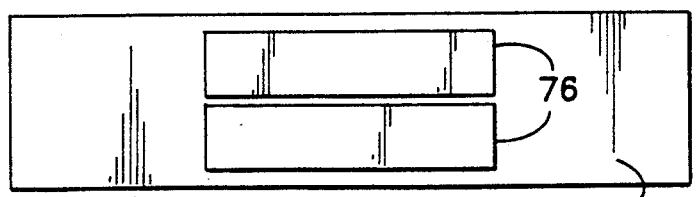
FIG. 10 is a plan view of the rear side of a removable shoulder board arranged for use with the spinal restraint device of this invention in situations where a transport by flexible stretcher may aggravate upper thorax injuries.

As seen best in FIGS. 2 and 4, the restraint device is provided with a piece of material 74 secured thereto behind the shoulder portion of the jacket. This material comprises one component of a hook end loop type Velcro fastener, the corresponding component 76 being provided on one side surface of a removable, rigid shoulder board 78, seen in FIG. 10. In the restraint device of this invention, the removable shoulder board finds utility only in situations where upper thorax and shoulder injuries are present and transportation by flexible stretcher is also involved. Since flexible stretchers tend to wrap about a patient as they are lifted and carried, it is advisable when such injuries are present to provide the rigid shoulder board which spans the distance behind and between the shoulders so that that portion of the flexible stretcher cannot be allowed to wrap inwardly and thereby exacerbate discomfort by applying inward compression on the thorax injury.

The attachment of the extrication and spinal restraint device of this invention is as follows: After access to an injured victim has been gained, and possible injuries have been determined, the spinal restraint device is unfolded into the open position of FIG. 4 and positioned behind the victim's back so that the central stitching 16 between the back brace boards 12 extends along the victim's spine. In the event of possible neck injury, a conventional cervical collar C is applied to the victim. While one rescuer manually supports and immobilizes the patient's head in a neutral in-line position, the restraint device is positioned behind the patient's back and the shoulder straps are attached in either the crossover manner or the over the shoulder manner described, depending on the injuries present. Next the torso straps are secured snugly but not tightly about the victim's chest and abdomen. Next the pelvis straps are secured in the manner previously described, and all straps are again adjusted to firmly immobilize the patient on the restraint device. With the device thus firmly attached, and with the one rescuer still maintaining the victim's head in position manually, the head pads, if required, are provided between the back of the victim's head and the backboards so that the head is maintained in the in-line position that had been maintained manually. The head flaps are then folded alongside the flat lateral planes of the head, and the forehead restraint strap is positioned over the forehead so that the disposable non-slip pad is against the patient's forehead. The forehead strap ends are pulled rearwardly and fastened to the head flaps 18 as described earlier, so that the tension of the forehead strap is sufficient to securely hold the victim's head immovably against the head pads between the side head flaps. In the event a rigid cervical collar has been applied, the lower head strap 36 is positioned over the collar and affixed to the side head flaps with sufficient tension to secure the lower portion of the head immovably. In the event that no cervical has been provided, the lower head strap is placed centrally over the nose, the strips 38 bridging the projecting portion of the nose as shown in FIGS. 1 and 3, the strap ends being secured to the side head flaps snugly enough to securely immobilize the lower portion of the head in position.

With the patient thus firmly immobilized, the straps are re-checked for proper tension, and the patient is removed to a stretcher for transport to a medical facility. It is to be noted that the particular positioning of the various straps on the jacket has been designed so that most of the interior chest remains uncovered to allow for chest auscultation and placement of EKG monitor leads without the need to readjust or remove any part of the immobilization device.

When the restraint device has been removed from a victim at a hospital, the straps may be folded and laid over the flexible side flaps and the flaps folded along the stitch lines 14 against the boards 12. The rigid board sections may then be folded along the central stitch line 16 so that the unit is compactly folded with all of the straps maintained inside the flexible side flaps. The resulting package is very compact in size, making the device extremely convenient to store. The discardable forehead pad 34 is removed from the forehead strap and replaced with a new one after each use to prevent contamination of personnel and future patients.

From the foregoing it is apparent to those skilled in the art that various changes may be made in the size, shape, type, number and arrangement of parts described hereinbefore without departing from the spirit of this invention and the scope of the appended claims. For example, although buckles and Velcro type fasteners have been illustrated herein, other suitable and conventional fastening means may alternatively be employed as desired. Also, other materials and jacket configurations may be employed as indicated in different general uses, as for example, uses commonly encountered with civilian extrications and injuries versus perhaps different particular needs and requirements more commonly encountered in military extrications and injuries.

Having thus described my invention and the manner in which it may be used, I claim:

1. A spinal restraint device for immobilizing the upper body of a person injured in a manner in which immobilization is indicated for extrication and transport from the scene of an accident or the like, the spinal restraint device comprising:
    a) a jacket of flexible material configured to extend substantially the length of a human's body from behind the head to approximately the base of the spine and to partially encircle the sides thereof,
    b) two elongated, parallel, rigid backboard members mounted on said flexible jacket for extension from behind the head to the base of the spine of a human body, the jacket mounting the backboard members with their confronting longitudinal edges disposed along the spine, the combined width of the backboard members being less than the width of a human torso or head, thereby forming a central, longitudinally extending rigid jacket portion,
    c) a pair of longitudinally and laterally flexible torso side flap members extending laterally from the sides of the rigid portion of the jacket and configured to extend flexibly along the sides of a human torso from adjacent the armpits downward to a point adjacent the hips,
    d) a pair of longitudinally and laterally flexible head side flap members extending laterally from the sides of the rigid head portion of the jacket and configured to extend flexibly along substantially the full length of the sides of a human head, the head flap members configured to receive head-securing strap means extending between and secured to the flap members for securely engaging and holding a human head positioned between the flap members and the backboard members,
    e) two longitudinally spaced, flexible torso strap means secured to said flexible torso flap members and configured to extend laterally across the front of a human torso for securing the opposite side torso flap members snugly against the sides of a torso,
    f) head-securing strap means configured to extend across the front of a human head for engagement with the opposite side flap members of the jacket for positively securing a head immovably against the rigid jacket portion between the head flaps,
    g) a pair of opposite pelvic-securing strap means configured to be secured at one of their ends to the rigid portion of the jacket for longitudinal extension downwardly therefrom a distance sufficient for the strap means to be drawn between the legs of a human body to its front side and be secured at their opposite ends to the opposite flexible side torso flap members, the strap means configured for extension specifically over the pelvis above the articulating joints of the hips, whereby articulation of the legs cannot effect movement of and changes in tension against the pelvic strap means and hence the jacket, and
    h) a pair of opposite upper torso-securing strap means each mounted on opposite sides of the jacket and configured to be fixedly secured at their opposite ends to a spaced point on the jacket below and behind the shoulders for securing the torso of a human body immovably to the jacket.

2. The spinal restraint device of claim 1 wherein the upper torso-securing strap means comprises a pair of upper torso securing strap means each secured to opposite sides of the flexible jacket and configured to extend across the upper torso in a crossover pattern for securing to respective opposite sides of the jacket to secure the upper torso positively and immovably in position.

3. The spinal restraint device of claim 2 wherein each said pair of upper torso securing strap means is further configured to extend about the shoulder area of a human torso and be secured to the same side of the jacket, whereby to secure individual associated shoulders immovably against the jacket to assure that potential upper thorax injuries are not immobilized in a collapsed position.

4. The spinal restraint device of claim 1 wherein each of said pair of pelvic-securing strap means comprises a pair of cooperating strap members configured for releasable and adjustable connection together, one end of one strap member being secured to the rigid portion of the jacket for longitudinal extension from the base of the backboards and configured to be drawn between the legs of a human body to its front side, the other strap member of each pair being attached at one of its ends to opposite lateral, flexible side torso flaps and positioned to extend around the front of the pelvis above the articulating joint of a hip for connection to and tensioning with the said first strap of the pair.

5. The spinal restraint device of claim 4 wherein the upper torso-securing strap means comprises a pair of upper torso securing strap means each secured to opposite sides of the flexible jacket and configured to extend across the upper torso in a crossover pattern for securing to respective opposite sides of the jacket to secure the upper torso positively and immovably in position.

6. The spinal restraint device of claim 5 wherein each of said pair of upper torso-securing strap means is further configured to extend about the shoulder area of a human torso and be secured to the same side of the jacket whereby to secure individual associated shoulders immovably against the jacket to assure that potential upper thorax injuries are not immobilized in a collapsed position.

7. The spinal restraint device of claim 1 wherein said head securing strap means comprises a forehead securing strap and a lower head-securing strap, the forehead strap removably mounting a moisture-absorbent foam type pad disposed on the strap and arranged to overlie a forehead to prevent slippage of the strap against the forehead and to absorb perspiration from the forehead.

8. The spinal restraint device of claim 1 wherein said head securing strap means comprises a forehead securing strap and a lower head-supporting strap, the lower head-supporting strap configured to positively engage the lower, fixed portion of a human skull, the strap comprising an elongated, flexible strap having an intermediate centrally open portion defining a pair of flexible strips arranged to bridge the projecting portion of a human nose therebetween and be secured at the strap ends to the head flap members to positively and removably secure a head without contacting or interfering with the mouth of a victim thus immobilized.

9. The spinal restraint device of claim 1 wherein said head securing strap means comprises a forehead securing strap and a lower head supporting strap, the lower head supporting strap configured to extend around a cervical collar positioned about the neck of a patient, the strap comprising an elongated, flexible strap having an intermediate centrally open portion defining a pair of flexible strips arranged to extend about the front of a cervical collar beneath the chin-supporting portion thereof, the strap ends configured for releasable attachment to the head flap members to positively and securely hold a head immovably in position thereagainst.

10. The spinal restraint device of claim 1 including removable, firm head pads configured for placement between the back of an upright human head and the rigid backboard members to accommodate for space that may otherwise be present therebetween when the head is secured in an upright position between the head flaps and backboard members of the restraint device.

11. The spinal restraint device of claim 1 including a removable, rigid shoulder support member arranged for releasable attachment to the back of the jacket with a human secured immovably therein, the shoulder support member configured to extend laterally across the back of the jacket to the opposite sides of the shoulders of a human torso, whereby to eliminate possible inward pressure against the shoulders that may otherwise occur in the normal use of a flexible type stretcher or the like.

* * * * *